United States Patent [19]

Lindmayer

[11] Patent Number: 4,979,935

[45] Date of Patent: Dec. 25, 1990

[54] METHOD OF PHOTODYNAMIC THERAPY EMPLOYING ELECTRON TRAPPING MATERIAL

[75] Inventor: Joseph Lindmayer, Potomac, Md.

[73] Assignee: Quantex Corporation, Rockville, Md.

[21] Appl. No.: 313,053

[22] Filed: Feb. 21, 1989

[51] Int. Cl.$^5$ .................... A61N 5/02; C07B 47/00; A61K 43/00
[52] U.S. Cl. ........................ 600/2; 540/145; 424/1.1
[58] Field of Search ............ 424/1.1, 4, 9; 604/20; 600/1-8; 128/898; 540/145; 428/690

[56] References Cited

U.S. PATENT DOCUMENTS

| | | | |
|---|---|---|---|
| 4,674,480 | 6/1987 | Lemelson | 600/4 |
| 4,755,324 | 7/1988 | Lindmayer | 252/301.4 S |
| 4,772,681 | 9/1988 | Fukuda et al. | 540/145 |
| 4,783,529 | 11/1988 | Lavallee et al. | 540/145 |
| 4,806,772 | 2/1989 | Lindmayer | 428/690 |
| 4,842,960 | 6/1989 | Lindmayer | 428/690 |
| 4,866,168 | 9/1989 | Dougherty et al. | 540/145 |
| 4,877,872 | 10/1989 | Morgan et al. | 540/145 |
| 4,879,186 | 11/1989 | Lindmayer | 428/690 |
| 4,883,790 | 11/1989 | Levy et al. | 540/145 |

OTHER PUBLICATIONS

Mew et al., "Photoimmunotherapy: Treatment of Animal Tumors with Tumor Specific Monoclonal Antibody-Hematoporphyrin Conjugates", Journal of Immunology, vol. 130, No. 3, Mar. 1983, pp. 1473-1477.
Weishaupt et al., "Identification of Singlet Oxgyen as the Cytotoxic Agent in Photo-Inactivation of a Murine Tumor", Cancer Research, vol. 36, pp. 2326-2329, Jul. 1976.

*Primary Examiner*—C. Fred Rosenbaum
*Assistant Examiner*—Sharon Rose
*Attorney, Agent, or Firm*—Ostrolenk, Faber, Gerb & Soffen

[57] ABSTRACT

A method of photodynamic therapy employing an electron trapping material as the light source. The electron trapping material is charged with light, which raises electrons in the material from a ground level to a higher trapping energy level. The material is then introduced into a patient's body, where it delivers light to and activates an antibody which has been retained in cancerous tissue. The electron trapping material can be either a deep trap or shallow trap phosphor. In the former case, stimulation of the charged material with infrared energy releases electrons from their traps, resulting in the emission of light within the patient's body. In the latter case, the material emits light immediately after charging with an intensity that decreases in inverse porportion to time. The electron trapping material may be provided in the form of a powder which can be inhaled for treatment of lung cancer, or suspended in a liquid which can be ingested, injected, or circulated in cavities of the body to treat other organs.

18 Claims, 4 Drawing Sheets

METHOD OF PHOTODYNAMIC THERAPY EMPLOYING ELECTRON TRAPPING MATERIAL

BACKGROUND OF THE INVENTION

Photodynamic therapy (PDT) is a cancer treatment modality in which cancer cells are destroyed through the energy represented by light photons. Typically, a light sensitive antibody made from cattle hemoglobin, called hematoporphyrin derivative (HpD), or a further purified mixture of HpD known as dihematoporphyrin ether/ester (DHE), is introduced into a patient's body. The antibody is purged from normal tissues during a latent period of 48–72 hours, but remains preferentially concentrated within malignant tissue. When the retained antibody is illuminated by light of a specific wavelength, it becomes excited and undergoes a spin conversion process in which energy is transferred to oxygen. The activated oxygen (known as singlet oxygen) is a highly reactive species which lethally damages cellular components - in this case, the surrounding malignant tissue Studies indicate that to achieve maximum tissue penetration during PDT, the wavelength of the activating light energy should be close to 630 nm. However, no presently available laser produces light at this specific wavelength. Therefore, PDT is typically performed by using an argon laser to pump a dye laser, which in turn is tuned to produce light having the desired wavelength of 630 nm. This results in bulky equipment and large electric power requirements.

The 630 nm activating light is ordinarily delivered through an optical fiber to a diffuser at the tumor tissue However, the use of an optical fiber during PDT is undesirably intrusive. Moreover, the effectiveness of PDT using an optical fiber is reduced when cancer cells are distributed over large organ surfaces or when the cancer cells are located in crevasses. In such cases, cancer cells cannot be fully illuminated even when a diffuser is employed.

In an effort to overcome the above-noted drawbacks, a peroxylate-based chemiluminescent agent has been suggested as a possible light source for PDT. However, this agent requires initiation by admixing harsh peroxides which cannot be tolerated by normal tissues.

SUMMARY OF THE INVENTION

The present invention is directed to a method of photodynamic therapy employing an electron trapping material as the light source The electron trapping material is adapted to release light at a wavelength which will activate a light sensitive antibody retained within cancerous tissue.

More specifically, the invention is directed to a method of photodynamic therapy including the steps of: (1) introducing an antibody into a patient's body which will be retained by cancerous tissue; (2) charging electron trapping material with light to raise electrons in the material from a ground state to a trapping energy level; (3) introducing the charged electron trapping material into a patient's body; and (4) activating the light sensitive antibody contained in cancerous tissue within the patient's body with light emitted from the electron trapping material when trapped electrons in the material fall from the trapping level back to the ground state.

The electron trapping material may be either a phosphor in which the raised electrons are held in deep traps until released by optical stimulation, or a phosphor with shallow traps which begins to emit light immediately after charging.

In a preferred embodiment of the invention, the electron trapping material is ground into a fine powder, and the particles are microencapsulated with an inert and transparent coating. Microencapsulation ensures that the electron trapping material will remain inert as it circulates through the patient's body.

In another embodiment of the invention, the electron trapping material is applied as a sheet to the patient's skin in the vicinity of cancerous tissue. The material charges up by exposure to ambient or artificial light, and emits light into the skin to activate the light sensitive antibody retained by the cancerous tissue. Again either a deep trap or shallow trap phosphor can be employed in this embodiment of the invention.

Since oxygen singlet production is accompanied by the release of light having a wavelength of 1.27 microns, the effectiveness of photodynamic therapy resulting from the method of the present invention can be indirectly determined by measuring the amount of light of this wavelength emitted at the site of the cancerous tumor.

BRIEF DESCRIPTION OF THE DRAWINGS

These and other features and advantages of the present invention will become apparent when the following text is read in conjunction with the accompanying drawings, in which.

DETAILED DESCRIPTION OF THE PREFERRED EMBODIMENTS

Figure 1:
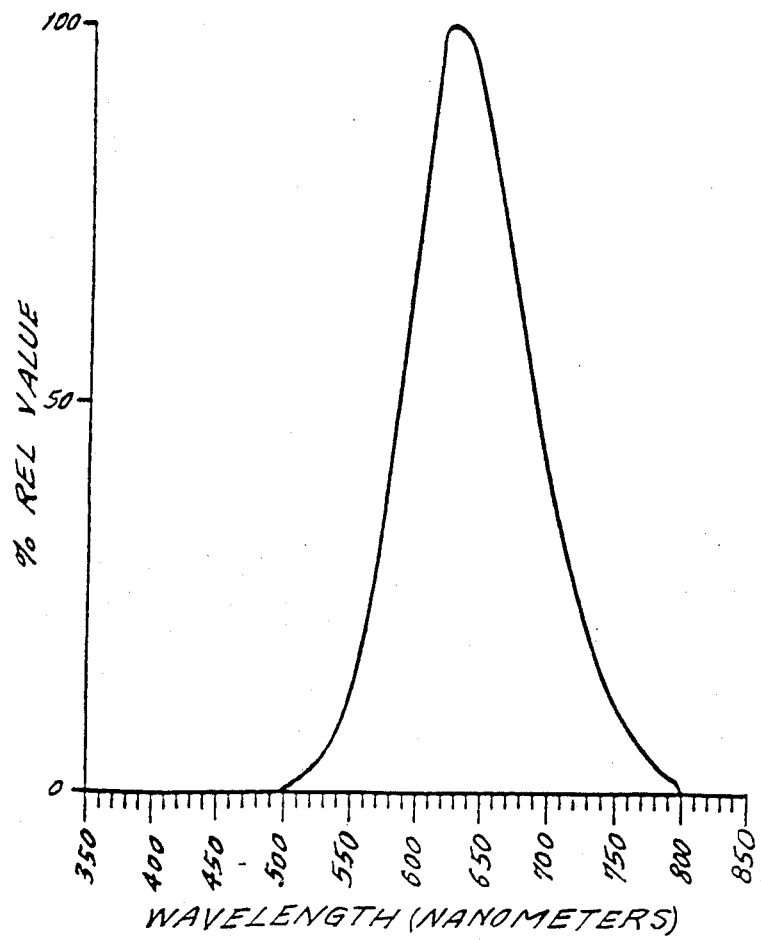
FIG. 1 shows the spectrum of light output by the deep trap phosphor which may be used in the present invention.

Luminescence refers to the ability of certain solids (and liquids) to emit light when driven by an external energy source. When the driving energy source is light, the proper term is photoluminescence. Within photoluminescence, numerous materials will emit light when driven by short wavelengths, such as ultraviolet. However, there is yet another interesting class of materials which, upon excitation by illumination, can store electrons in "traps" for various lengths of time.

In the case of deep traps (on the order of 1.2 eV), trapped electrons can be released at a later time by photons having an energy similar to the depth of the trap (thermal discharging is negligible). Under these circumstances, it appears that light has been "stored" for later use; emission of visible light can only be activated by infrared.

In the case of shallow traps (on the order of 0.1 eV), spontaneous emission occurs (which produces phosphorescence or "afterglow" because the thermal agitation is sufficient to excite electrons out of the traps.

The invention is made possible by the development of the above-noted electron trapping (ET) materials by the assignee of the present application. In particular, certain deep trap and shallow trap materials have been developed which emit the proper wavelength, 630 nm, to activate the cancer destroying HpD and DHE antibodies.

The deep trap ET material used in the present invention is described and claimed in U.S. Pat. No. 4,806,772, the disclosure of which is here incorporated by reference. The deep trap ET material comprises a base material, a first dopant, and a second dopant. The base material may be selected from the group of alkaline earth metal sulfides such as strontium sulfide. The first dopant is samarium and the second dopant is selected from the group of europium oxide, europium fluoride, europium chloride, and europium sulfide. Barium sulfate is preferably added to improve light output and a fusible salt such as lithium fluoride is useful in certain embodiments.

An exemplary composition for the deep trap ET material is as follows:

| Strontium sulfide | 100 parts |
|---|---|
| Barium sulfate | 5.5 parts |
| Lithium fluoride | 5.5 parts |
| Samarium | 150 parts per million |
| Europium oxide | 550 parts per million |

As used above and throughout this application, "parts" and "parts per million" shall refer to parts by weight unless otherwise noted.

The mixture is placed into a graphite crucible within a furnace flushed with a dry nitrogen atmosphere (derived from a liquid source) or other dry inert atmosphere such as argon, and heated to between 1150° C. and 1300° C. (preferably 1200° C) for 30 minutes to one hour such that a fused mass is formed. For longer heating times, the fused mass could be formed at temperatures as low as 950° C. Temperatures as high as 2000° C. could be used to form such a fused mass in shorter times.

After cooling, the fused mass is ground using standard techniques into a fine powder having a particulate size of 1 to 100 microns.

After grinding, the powdered material is heated to about 300° C. to 700° C. (preferably 600° C.) in the graphite crucible within the nitrogen or other inert atmosphere furnace. This second heating is below the fusing temperature of the material (about 700° C.) and is maintained for 10 to 60 minutes (preferably 30 minutes). This second heating step removes internal stresses and repairs damage done to the crystalline surfaces during the grinding step.

In the above mixture, the strontium sulfide serves as a base material, whereas the lithium fluoride operates to provide the fusibility characteristics. Alternatively, other alkaline earth metal sulfides might be used as the base material.

The barium sulfate in the above mixture is used to improve the brightness of output light from the material. Preferably 5.5 parts are used as noted above, but between 1 and 10 parts may be used of the barium sulfate as well as between 1 and 10 parts of lithium fluoride relative to the 100 parts of strontium sulfide. The barium sulfate is not absolutely essential, but will greatly improve the optical characteristics of the material.

The samarium and europium oxide in the above mixture are used for establishing the communication band and the electron trapping level. Preferably 150 parts per million of samarium are used, but the samarium could alternately be between 50 parts per million and 300 parts per million. The europium oxide may be between 300 and 800 parts per million with 400 and 600 parts per million being preferred and 550 parts per million being the optimal value. Europium fluoride, europium chloride, or europium sulfide could be used in lieu of europium oxide.

Figure 2:
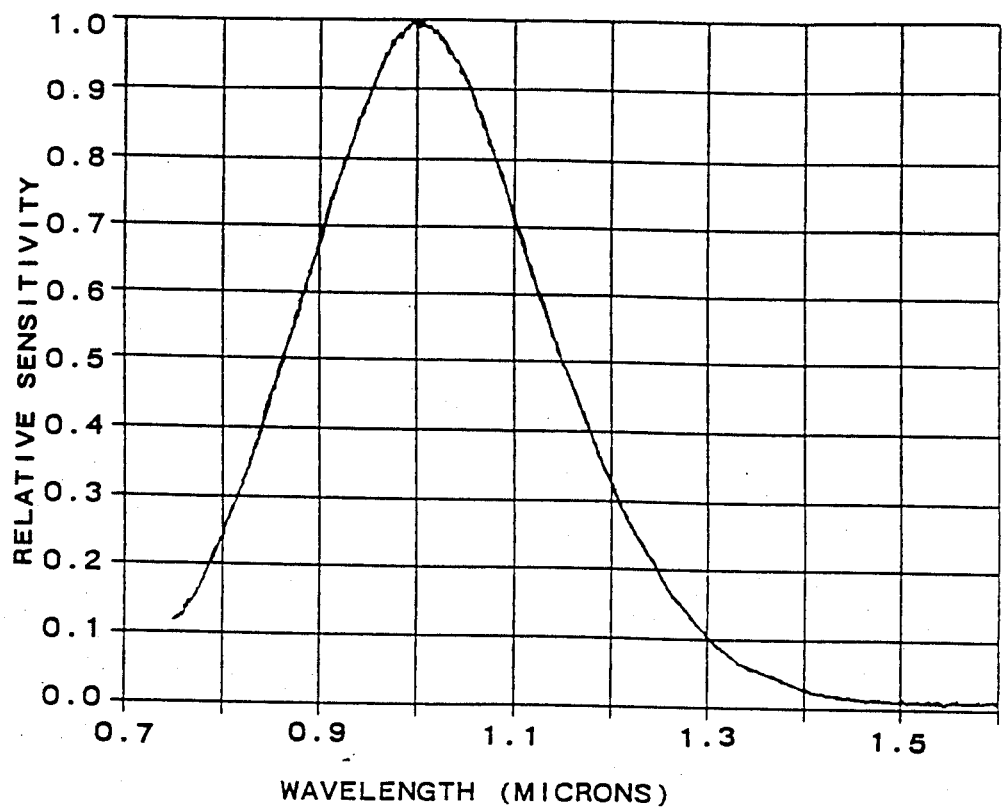
FIG. 2 shows the infrared interrogation response of the deep trap phosphor which may be used in the present invention.

The mixture resulting from the above process provides a depth for electron traps of 1.2 electron volts below the communication band and has an output spectrum as shown in FIG. 1, which illustrates that the center frequency of the output has a wavelength of approximately 630 nanometers corresponding to orange light. The infrared interrogation response of the mixture is shown in FIG. 2.

The present invention can also be used with a deep trap ET material having a base material comprised of a mixture of two alkaline earth metal sulfides, such as a mixture of strontium sulfide and calcium sulfide. This mixed base deep trap phosphor is described and claimed in U.S. Pat. No. 4,842,960, the disclosure of which is herein incorporated by reference.

The use of a mixture of two alkaline earth metal sulfides as the base material significantly improves the light output as will be discussed subsequently. A third dopant selected from the group of cerium oxide, cerium fluoride, cerium chloride and cerium sulfide can also be added to provide a 10 percent improvement in performance over materials with only the other two dopants.

An exemplary mixture of a deep trap ET material with a mixed base is as follows:

| Strontium sulfide | 69 parts |
|---|---|
| Calcium sulfide | 25 parts |
| Samarium | 150 parts per million |
| Europium oxide | 500 parts per million |
| Cerium sulfide | 500 parts per million |
| Lithium fluoride | 5.7 parts |

Figure 3:
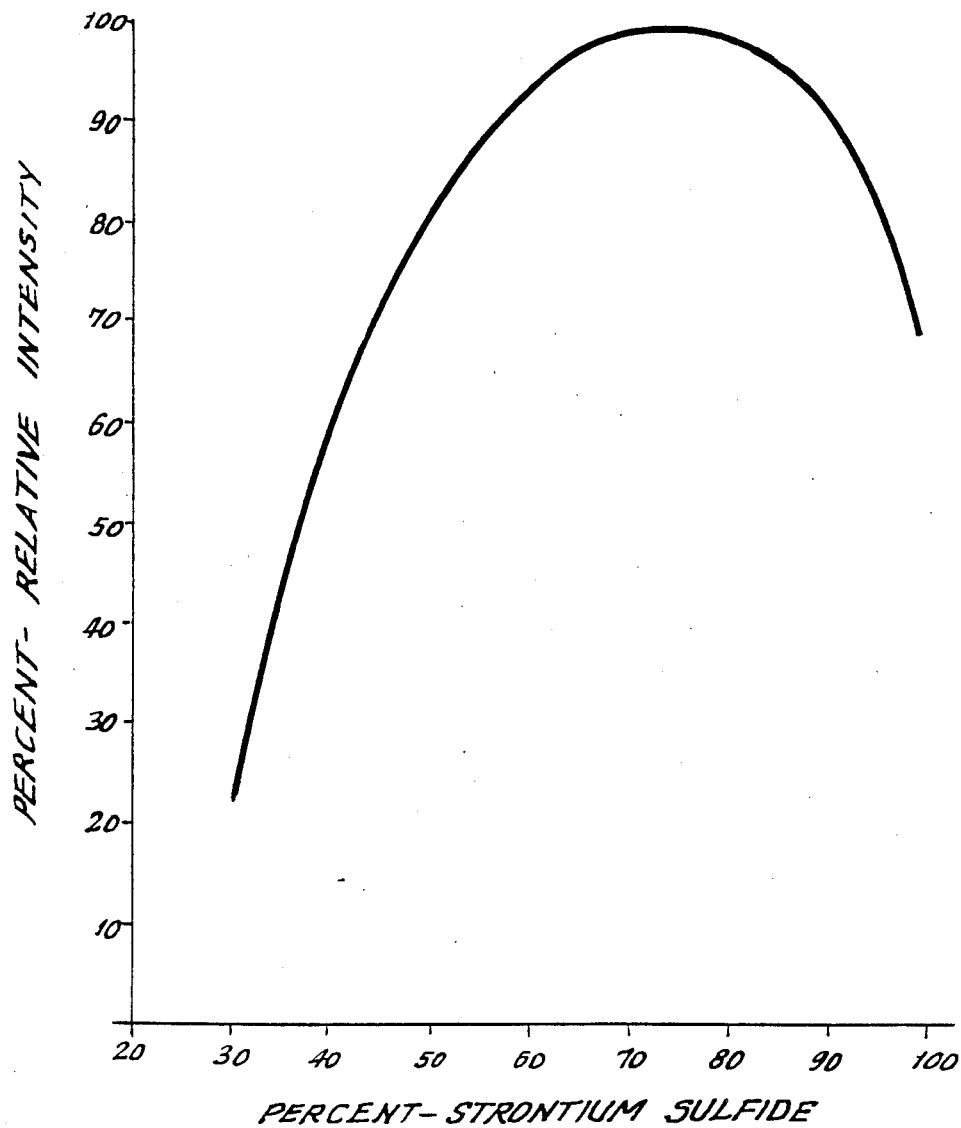
FIG. 3 shows the relative performance of the mixed base deep trap phosphor which may be used in the present invention.

The light output, and thereby the efficiency, is very much improved by the proper mixture of two sulfides FIG. 3 shows the relative performance of the optical material as a function of strontium and calcium sulfide ratios. At 100 percent strontium sulfide, the intensity is approximately 70 percent of peak intensity which is experienced with the ratio of the above example.

The two sulfides apparently form a new crystal (ternary compound). This basic change in the base crystal significantly improves the performance of the optical material. This improvement is apparent when the samarium/europium impurity pair is used without a cerium compound. The introduction of a cerium compound further enhances the efficiency.

As in the first example, the dopants are used for establishing the communication band and the electron trapping level. As before, preferably 150 parts per million of samarium are used, but the samarium could alternatively be between 50 parts per million and 500 parts per million, depending on the specific application. The europium and cerium compound concentrations may be between 100 and 1000 parts per million with 200 and 600 parts per million being preferred and 500 parts per million being the optimal value.

The process for making the material is the same as that described for the first example, and yields a substance with electron trap depths of about 1.2 electron volts below the communication band and an output spectrum as shown in FIG. 1 with a center frequency of approximately 630 nanometers corresponding to an orange light.

The shallow trap ET material used in the present invention is described and claimed in U.S. Pat. No. 4,755,324, issued July 5, 1988, the disclosure of which is herein incorporated by reference. Briefly, the shallow trap ET material comprises a base material selected from the group of alkaline earth metal sulfides, preferably strontium sulfide, two dopants, preferably lanthanum oxide and europium trioxide, and fusible salt such as lithium fluoride. The material provides electron trapping with trap depths less than 0.150 eV and more than 0.020 eV.

An exemplary mixture for the shallow trap ET material is as follows:
96% SrS
3% LiF
3000 ppm LaO
750 ppm $Eu_2O_3$ The preferred concentration ranges of the components and other exemplary mixtures are set forth in U.S. Pat. No. 4,755,324 and will not be repeated here.

To form the material, the components are combined and the mixture is heated to about 1,000° C. in a furnace in an atmosphere of dry nitrogen to form a fused mass.

The fused mass is ground to a fine powder having particle size in the order of 50 microns or less.

Figure 4:
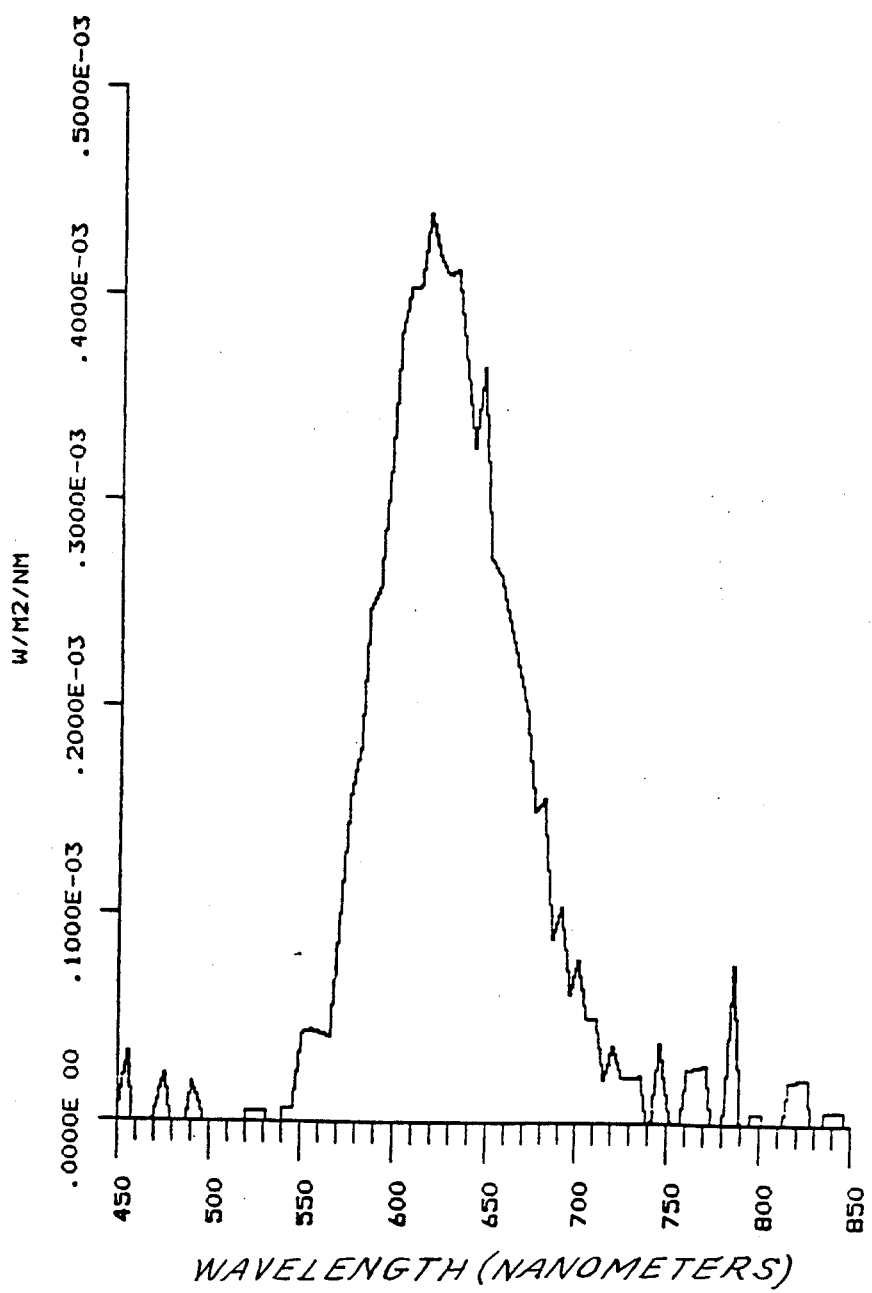
FIG. 4 shows the spectrum of light output by the shallow trap phosphor which may be used in the present invention.

After grinding, the powdered material is heated at about 600° C. and below fusing temperature for 30 minutes. The resultant material has the emission spectrum of FIG. 4.

In general, afterglow of the material is temperature dependent, and the afterglow intensity decreases approximately inversely with time as a function of 1/time.

The above-described deep trap and shallow trap ET materials emit a spectrally narrow bandwidth of light around 630 nm, which surrounds the critical wavelength necessary to inactivate the HpD and DHE antibodies. Since the electron trapping materials appear in the form of a fine powder when made in accordance with the above-described processes, they can be introduced as a light source into the body in numerous ways. In essence then, it becomes possible to drink, inhale, or circulate in cavities of the body an orange light. Thus, the present invention for the first time provides the critical wavelength through internal illumination.

The literature speaks about PDT treatments of patients with promising results involving cancerous tumors at various locations. If the ET particles are suspended in liquid, the esophagus, the stomach and the gastrointestinal tract in general could be illuminated internally. The liquid could also be pumped or circulated through the patient's body as a light "conveyor belt", transporting light from outside the body to the treatment area within, and then being circulated outside again to be recharged with light and sent back into the body.

The lung of a patient could be illuminated by inhalation of a fine ET powder, a process that could continue for a relatively long time without discomfort. Other organs of the body could be reached in analogous ways, depending upon the location and type of tissue surrounding the cancer—the common denominator of all these methods, however, is the use of the electron trapping material as the vehicle to illuminate an antibody that has been retained at the treatment site.

If a deep trap material is employed, the ET particles are charged up with ambient light before intake. Once the material is inside, the patient is exposed to infrared light, such as from an infrared lamp The infrared stimulation releases the trapped electrons, resulting in the desired emission of 630 nm light. Since the deep trap ET material holds its charge for up to a week, and since only a portion of the electrons are released from their traps upon infrared stimulation, multiple treatments are possible after each intake of ET material. Obviously, if the material is circulated through an organ or crevice of the body, an unlimited amount of light can be delivered internally.

If a shallow trap material is employed, it is charged up with light immediately before intake and phosphorescence occurs inside the patient's body with a time decay approximately following a 1/t function.

Obviously, the size of the ET particles depends upon the particular method of intake. If the material is inhaled, it must be ground into a fine powder. If it is suspended in liquid for ingestion, injection or circulation, the optimum particle diameter is between 10-20 microns. A small particle size can more easily penetrate the interstices of cancerous tissue, but the intensity of emitted light from the ET material falls off when the particles are smaller than 10 microns in diameter.

The electron trapping particles used in the present invention are chemically stable crystallites. Nevertheless, it is desirable to microencapsulate the individual particles to ensure inertness within the body.

Preferred materials for microencapsulation are organometallic compounds because they produce materials which are very inert and very transparent and which readily coat the particulate photoluminescent materials described above. Certain organometallic compounds contain a metal oxide and an organic molecule. When the organometallic compound is heated to temperatures of about 400°-500° C., the organic molecule disintegrates leaving only the metal oxide. Preferred inert and transparent metal oxides available in an organometallic form are $SiO_2$, $Ta_2O_5$, $Nb_2O_5$, and $TiO_2$. The particles (or crystallites) of electron trapping material are easily coated with such oxides. Besides inertness, encapsulation reduces surface recombination (a loss mechanism) and improves optical coupling. Microencapsulation may be accomplished by techniques which are known per se, e.g., spray techniques, direct oxide deposition, vacuum evaporation, chemical vapor deposition, and sputtering.

The optimum size of the microencapsulated particles is a function of the sedimentation rate of the microencapsulated particles in liquid suspension, the light emission characteristics of the electron trapping material, and the ability of the microencapsulated particles to penetrate the interstices of cancerous tissue. A preferred diameter is 50 microns.

The electron trapping material can also be applied as a sheet to the patient's skin in the vicinity of cancerous tissue. The material charges up by exposure to ambient or artificial light and emits light of the desired 630 nm wavelength into the patient's skin to activate the light sensitive antibody retained by the tumor.

In yet another embodiment, the electron trapping material is encapsulated in an autoclavable clear binder and bonded to the tip of an optical fiber. The optical fiber is then placed adjacent the cancerous tissue, and infrared stimulating light (such as from a laser diode) is sent through the fiber to release 630 nm illumination from the ET material. Although more intrusive than the previously described methods, this still avoids the requirement of using argon/dye lasers and their associated bulk and high power usage.

Since oxygen singlet production is accompanied by the release of light having a wavelength of 1.27 microns, the effectiveness of photodynamic therapy resulting from the method of the present invention can be indirectly quantified by measuring the amount of light of this wavelength emitted at the site of the cancerous tissue. Such light can be detected by a photomultiplier specially adapted for infrared sensitivity ("an infrared photomultiplier"), such as described in U.S. Patent Application Ser. No. , filed on even date herewith, now allowed assigned to the present assignee. Briefly, an infrared photomultiplier is an ordinary photomultiplier tube fitted with a special upconverting faceplate which converts incoming infrared light (to which the photomultiplier tube is relatively insensitive) into visible light (to which photomultiplier tube is highly sensitive). A long wavelength filter is employed to prevent external visible light (in this case the orange light emitted during PDT) from reaching the photomultiplier. Thus, the infrared photomultiplier is sensitive only to infrared light.

The upconverting faceplate is comprised of a deep trap ET material doped with a europium compound similar to that described above in the first example. To reduce phosphorescence of the material, the barium sulfate is exchanged for strontium carbonate, and the mixture is fused at 1300° C., rather than 1200° C.

Alternatively, a deep trap ET similar to that described and claimed in U.S. Pat. No. 4,879,186, can be used for the upconverting faceplate. This material is also europium doped, but has a calcium sulfide base, rather than a strontium sulfide base. This substitution of base material results in a shift of IR sensitivity to longer wavelengths (peaking at about 1150 nm and having about 50 percent output at the desirable wavelength of 1270 nm). Again, to reduce phosphorescence, the barium sulfate in the material is exchanged for strontium carbonate, and the mixture is fused at 1300° C., rather than 1100° C.

Accordingly and in summary, the method of the present invention provides an internal light source which:

(1) vastly expands the potential use and effectiveness of photodynamic therapy because of its ability to reach crevices of the body in liquid form;

(2) has minimal cost when compared to bulky laser equipment required to produce the required 630 nm wavelength;

(3) requires no tuning because the 630 nm wavelength is automatically produced by the crystal structure and dopants;

(4) assures light radiation of malignant tissue in many cases without intrusion into the body; and (5) is portable and allows for widespread use away from large institutions because the material is energized by sunlight or ambient light, not by electricity.

Although the present invention has been described in connection with preferred embodiments thereof, many variations and modifications will now become apparent to those skilled in the art. It is preferred, therefore, that the present invention be limited not by the specific disclosure herein, but only by the appended claims.

What is claimed is:

1. A method of photodynamic therapy, comprising the steps of:

(a) introducing a light sensitive antibody comprising hematoporphyrin derivative or dihematoporphyrin ether/ester in a patient's body which will be retained by cancerous tissue;

(b) charging particulate electron trapping phosphor material with optical energy, said optical energy raising electrons in said material from a ground level to a trapping level;

(c) introducing said charged particulate electron trapping material into a patient's body such that it becomes disposed adjacent said cancerous tissue; and (d) activating said antibody with light released by said charged particulate electron trapping phosphor material as said electrons fall from said trapping level back to said ground level, said activated antibody releasing singlet oxygen which destroys said cancerous tissue.

2. A method of photodynamic therapy as recited in claim 1, wherein said electron trapping phosphor material comprises a deep trap phosphor which releases light upon optical stimulation, and wherein said method comprises the additional step of applying said optical stimulation after said deep trap phosphor has been introduced into the patient's body.

3. A method of photodynamic therapy as recited in claim 2, wherein said charging optical energy comprises visible light and said optical stimulation comprises infrared light.

4. A method of photodynamic therapy as recited in claim 3, wherein said light released by said charged particulate material is orange light with a wavelength of about 630 nm.

5. A method of photodynamic therapy as recited in claim 2, wherein said deep trap phosphor comprises a base of strontium sulfide doped with samarium and a europium compound.

6. A method of photodynamic therapy as recited in claim 2, wherein said deep trap phosphor comprises a base of strontium sulfide and calcium sulfide doped with samarium and a europium compound.

7. A method of photodynamic therapy as recited in claim 6, further comprising a cerium compound dopant.

8. A method of photodynamic therapy as recited in claim 1, wherein said electron trapping phosphor material comprises a shallow trap phosphor which spontaneously emits light immediately after being charged, the intensity of said emitted light decreasing approximately in inverse proportion to time.

9. A method of photodynamic therapy as recited in claim 8, wherein said charging optical energy comprises visible light and said emitted light comprises orange light with a wavelength of about 630 nm.

10. A method of photodynamic therapy as recited in claim 8, wherein said shallow trap phosphor comprises a base of strontium sulfide doped with lanthanum oxide and europium trioxide.

11. A method of photodynamic therapy as recited in claim 1, wherein said particles of electron trapping phosphor material are individually encapsulated with an inert and transparent coating before being introduced into the patient's body.

12. A method of photodynamic therapy as recited in claim 1, wherein said step of introducing the electron trapping phosphor material into the patient's body comprises suspending the material in a liquid and having the patient drink the liquid.

13. A method of photodynamic therapy as recited in claim 1, wherein said step of introducing the electron trapping phosphor material into the patient's body comprises suspending the material in a liquid and injecting it into the patient's body.

14. A method of photodynamic therapy as recited in claim 1, wherein said step of introducing the electron trapping phosphor material into the patient's body comprises suspending the material in a liquid and circulating the liquid through a cavity of the patient's body.

15. A method of photodynamic therapy as recited in claim 1, further comprising the step of measuring the effectiveness of said therapy by detecting and measuring the infrared energy released by singlet oxygen production.

16. A method of photodynamic therapy as recited in claim 15, wherein a photomultiplier adapted to be sensitive to infrared radiation and insensitive to visible light is used to detect said infrared energy emitted during singlet oxygen production.

17. A method of photodynamic therapy as recited in claim 2, wherein said deep trap phosphor is introduced in the patient's body on the tip of an optical fiber, and said optical stimulation is applied through said optical fiber.

18. A method of photodynamic therapy, comprising the steps of:
    (a) introducing a light sensitive antibody comprising hematoporphyrin derivative or dihematoporphyrin ether/ester into a patient's body which is retained by cancerous tissue;
    (b) charging particulate electron trapping phosphor material with optical energy, said optical energy raising electrons in said material from a ground level to a trapping level;
    (c) applying said charged particulate electron trapping phosphor material as a sheet onto a patient's body near said cancerous tissue; and
    (d) activating said antibody with light released by said charged particulate electron trapping phosphor material as said electrons fall from said trapping level back to said ground level, said activated antibody releasing singlet oxygen which destroys said cancerous tissue.

* * * * *